(12) United States Patent
Dedhar et al.

(10) Patent No.: US 7,863,429 B2
(45) Date of Patent: Jan. 4, 2011

(54) TREATMENT OF INFLAMMATORY DISEASES INCLUDING PSORIASIS

(75) Inventors: Shoukat Dedhar, North Vancouver (CA); Greg Hannigan, Toronto (CA); David W. C. Hunt, Surrey (CA); Jing-Song Tao, Vancouver (CA); Ladan Fazli, North Vancouver (CA)

(73) Assignees: QLT Inc., Vancouver, British Columbia (CA); Sunnybrook and Women's College and Health Science Centre, North York, Ontario (CA)

( * ) Notice: Subject to any disclaimer, the term of this patent is extended or adjusted under 35 U.S.C. 154(b) by 1267 days.

(21) Appl. No.: 09/998,250

(22) Filed: Nov. 30, 2001

(65) Prior Publication Data

US 2002/0155179 A1 Oct. 24, 2002

(51) Int. Cl.
*C07H 21/02* (2006.01)
(52) U.S. Cl. ..................... 536/23.1
(58) Field of Classification Search ............... 514/178, 514/232.5, 231.5; 536/23.1; 435/325, 320
See application file for complete search history.

(56) References Cited

U.S. PATENT DOCUMENTS

| 5,378,725 A * | 1/1995 | Bonjouklian et al. | 514/453 |
| 6,001,622 A | 12/1999 | Dedhar et al. | |
| 6,046,224 A * | 4/2000 | Natarajan et al. | 514/381 |
| 6,214,813 B1 * | 4/2001 | Zhang et al. | 514/150 |
| 6,291,447 B1 * | 9/2001 | Andersen et al. | 514/183 |

FOREIGN PATENT DOCUMENTS

| WO | WO 94/21781 | 9/1974 |
| WO | 96/00760 | 5/1996 |
| WO | WO 96/36642 | 11/1996 |

OTHER PUBLICATIONS

Robbins Pathological Basis of Disease, 1994, W.B. Saunders Company, 5th edition, pp. 75-84.*
Zhang et al. (Up-regulation of phophatidylinositol 3-kinase in psoriatic lesion, 1999, Chinese Medical Journal, vol. 112, iss. 12, pp. 1097-1100).*
Dedhar, Shoukat, "Integrin Mediated Signal Transduction In Oncogenesis: An Overview," *Cancer and Metasis Reviews* (1995) vol. 14:165-172.
Dedhar and Hannigan, "Integrin Cytoplasmic Interactions and Bidirectional Transmembrane Signaling," *Current Opinion Cell Bio.* (1996) vol. 8:559-657.
Gimond et al., *Exp. Cell Res.*, (1995) vol. 216:232-235.
Hannigan et al., "Regulation of Cell Adhesion and Anchorage Dependent Growth By A New Betal Integrin Linked Protein Kinase," *Nature* (1996) vol. 379:91-96.
Hannigan et al., "Overexpression of A Novel Integrin Linked Kinase (ILK) Induces a Transformed Phenotype and Cyclin D1 Expression," *Molecular Biology of the Cell* (Nov. 1995) vol. 6:2244 XP000673935.

(Continued)

*Primary Examiner*—San-ming Hui
(74) *Attorney, Agent, or Firm*—Bozicevic, Field & Francis LLP; Pamela J. Sherwood

(57) ABSTRACT

Inhibitors of integrin-linked kinase (ILK) are used in the treatment of inflammatory disease, including cutaneous inflammatory diseases, such as psoriasis, scleroderma, systemic lupus erythematosus and atopic dermatitis.

7 Claims, 3 Drawing Sheets

Normal skin - Sample 1 (x10 magnification)

KL   EP-KC   BL   DV

Psoriatic Skin - Patient 1 (x10 magnification)

KL   EP-KC   BL   DV

OTHER PUBLICATIONS

Hannigan et al., "Cloning of a Novel Protein Kinase Associated With Beta 1 Integrin Cytoplasmic Tails," 86th *Annual Meeting of the American Association for Cancer Research* (Mar. 1995) p. 361, XP000673939.

Kappel, Catherine A. et al., (1992) *Current Opinion in Biotechnology* vol. 3:548-553.

Lin, Tsung H. et al., "Integrin-Mediated Tyrosine Phosphorylation and Cytokine Mesage Induction in Monocytic Cells," *The Journal of Biological Chemistry* (Jul. 7, 1995) vol. 270, No. (27):16189-16197.

Jacq et al., (1994) *Cell* vol. 79, No (1):107-117.

Miyamoto, Shingo et al., "Synergistic Roles for Receptor Occupancy and Aggregation in Integrin Transmembrane Function," *Science* (Feb. 10, 1995) vol. 267:883-885.

Palmiter er al., (Nov. 1983) *Science* vol. 222:809-814.

Pursel, V.G. et al., (1990) *J. Reprod. Fert., Suppl.* vol. 40:235-245.

Morino et al., "Matrix-Integrin Interaction Activates the Mitogen Activated Protein Kinase p44erk, 1 and p42erk-2," *J. Biological Chemistry* (1995) vol. 270:269-273.

Rosales, Carlos et al., "Signal Transduction By Cell Adhesion Receptors," *Biochimica et Biophysica Acta* (1995) vol. 1242:77-98.

Lipfert. et al., (1992) *J. Cell Biol.* vol. 199:905-912.

* cited by examiner

FIG. 1A
Normal skin - Sample 1 (x10 magnification)

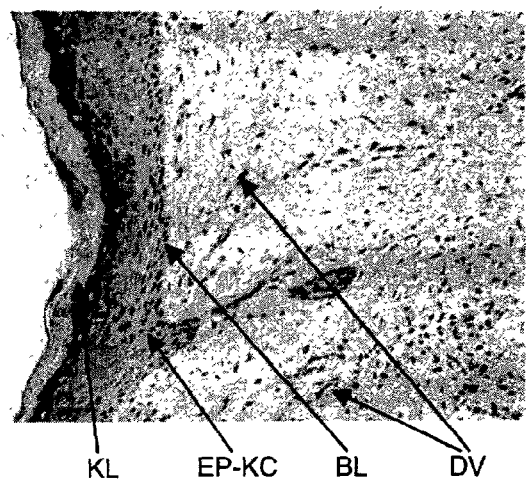

FIG. 1B
Psoriatic Skin - Patient 1 (x10 magnification)

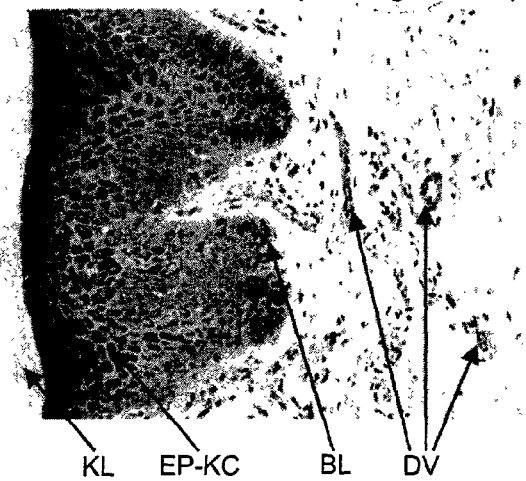

FIG. 1C
Normal skin - Sample 2 (x10 magnification)

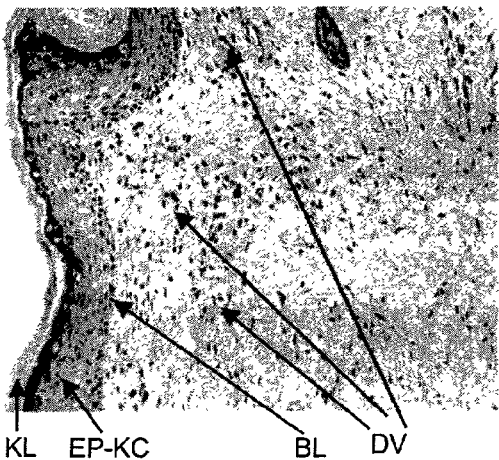

FIG. 1D
Psoriatic Skin - Patient 1 (x10 magnification)

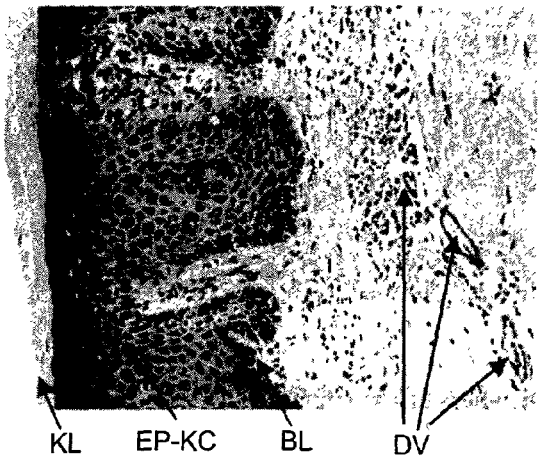

FIG. 1E
Normal skin - Sample 1 (x20 magnification)

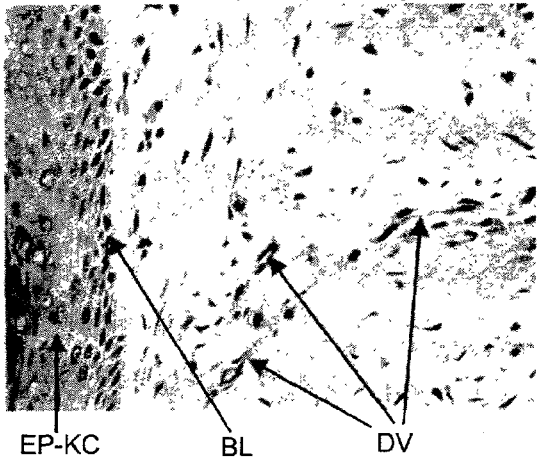

FIG. 1F
Psoriatic Skin - Patient 2 (x20 magnification)

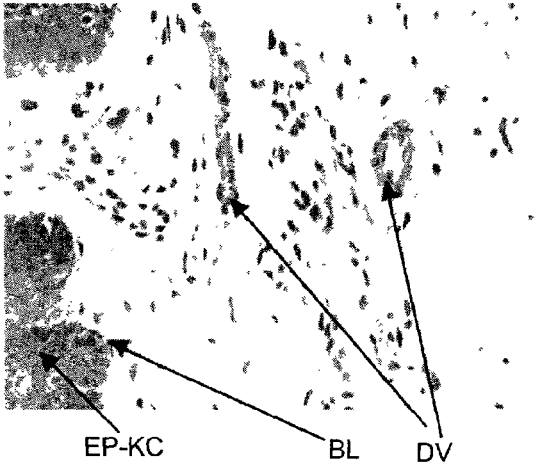

ILK staining of normal and psoriatic skin section. BL=Bruch's membrane, DV=dermal vasculature, EP-KC=epidermal keratinocytes, KL=keratin layer

FIG. 2A

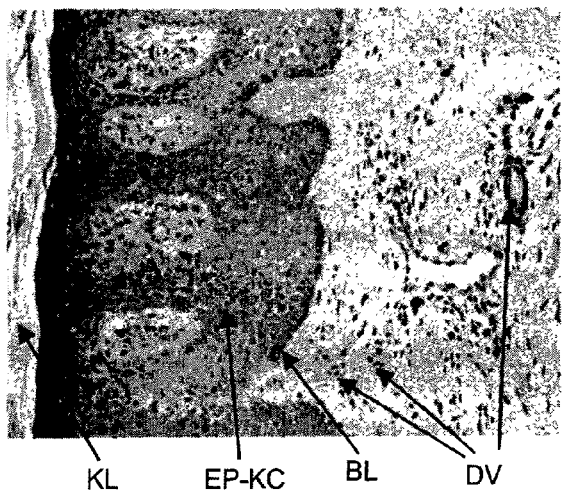

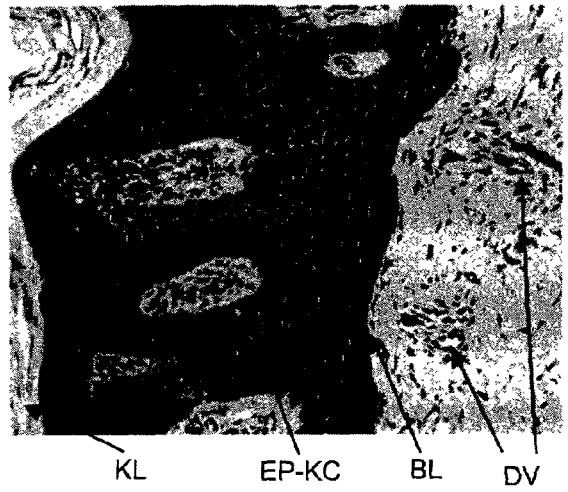

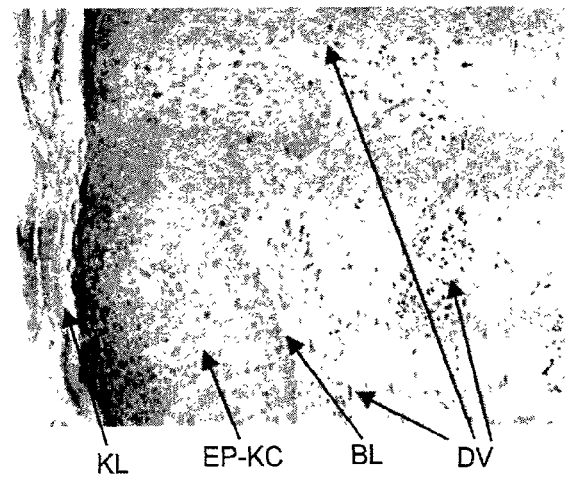

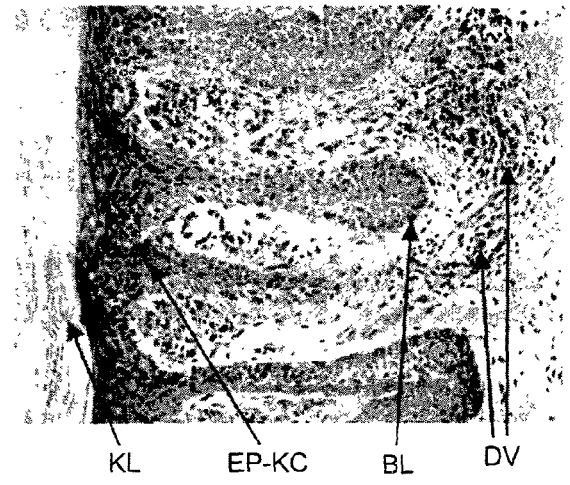

KL  EP-KC  BL  DV

ILK expression in epidermal keratinocytes and dermal vascular endothelium correlates with psoriatic disease progression. All sections were stained under similar experimental conditions at the same time. Antibody concentrations were 1:1000 dilutions. All photographs were taken at 10x magnification. EP-KC = epidermal keratinocytes, KL = keratin layer, BL = basal layer, DV = dermal vasculature Mouse Ear Edema Model
ICD-014

TREATMENT OF INFLAMMATORY DISEASES INCLUDING PSORIASIS

TECHNICAL FIELD

The invention relates to the use of inhibitors of integrin-linked kinase (ILK) in the treatment of inflammatory diseases and autoimmune conditions such as psoriasis in which the immune system directly contributes to disease pathogenesis.

BACKGROUND OF THE INVENTION

Psoriasis is a chronic skin disease, characterized by scaling and inflammation. Psoriasis affects 1.5 to 2 percent of the United States population, or almost 5 million people. It occurs in all age groups and about equally in men and women. People with psoriasis suffer discomfort, restricted motion of joints, and emotional distress. When psoriasis develops, patches of skin thicken, redden, and become covered with silvery scales, referred to as plaques. Psoriasis most often occurs on the elbows, knees, scalp, lower back, face, palms, and soles of the feet. The disease also may affect the fingernails, toenails, and the soft tissues inside the mouth and genitalia. About 10 percent of people with psoriasis have joint inflammation that produces symptoms of arthritis.

When skin is wounded, a wound healing program is triggered, also known as regenerative maturation. Lesional psoriasis is characterized by cell growth in this alternate growth program. In many ways, psoriatic skin is similar to skin healing from a wound or reacting to a stimulus such as infection, where the keratinocytes switch from the normal growth program to regenerative maturation. Cells are created and pushed to the surface in as little as 2-4 days, and the skin cannot shed the cells fast enough. The excessive skin cells build up and form elevated, scaly lesions. The white scale (called "plaque") that usually covers the lesion is composed of dead skin cells, and the redness of the lesion is caused by increased blood supply to the area of rapidly dividing skin cells.

Human epidermal keratinocytes express several adhesive receptors that belong to the integrin family of α/β heterodimers. Several of the keratinocyte integrins share a common $\beta_1$ subunit. $\beta_1$ integrins not only mediate keratinocyte adhesion to extracellular matrix proteins, but also play a role in intercellular adhesion, lateral migration, stratification, proliferation and the regulation of terminal differentiation. Integrin expression is largely confined to the basal, proliferative, layer of keratinocytes in normal adult skin, although in psoriatic lesions suprabasal keratinocytes co-express integrins. Suprabasal integrin expression has also been noted in eczema and lichen planus.

The chronic skin inflammation of psoriasis is associated with hyperplastic epidermal keratinocytes and infiltrating mononuclear cells, including CD4+ memory T cells, neutrophils and macrophages. Because of this highly mixed inflammatory picture and the resulting complex interrelationships between these different cells, it has been very difficult to dissect the mechanisms that underlie the induction and progression of the disease.

The instigating factors for psoriasis are poorly defined, although it evident that it is a T cell-mediated autoimmune condition. T cells are present throughout the epidermis and at a markedly high density on the dermal side of the epidermal-dermal junction. Within the epidermis, $CD8^+$ cytotoxic T cells are more highly represented than $CD4^+$ helper T cells. Activated T lymphocytes elaborate factors that drive the character of the psoriatic plaque. Psoriasis is considered a multigene disease although disease expression is due in part to environmental factors. Physical trauma, emotional stress, infection or certain medications may contribute to the psoriatic condition. The genetic association with psoriasis is strongest with the major histocompatibility complex (MHC) Class I allele HLA-Cw6 and to a lesser extent the MHC Class II allele HLA-DR7. This observation suggests that psoriasis pathogenesis may result from the recognition of a local peptide antigen presented by resident skin cells in the context of MHC Class I molecules to auto-reactive $CD8^+$ T cells.

Although psoriasis is not life threatening, the social stigma and reduction in quality of life associated with disease are profound issues for these patients and their families. Currently, there is no long-term cure for psoriasis. Established anti-psoriasis therapies have been grouped into suppressive and remittive types. Suppressive therapies include coal tar preparations (natural coal tar or the distillate anthralin), topical corticosteroids, mechanical treatments to remove scale, and antimetabolites such as methotrexate. For remittive therapy, the photosensitizing drug, psoralen, combined with long wavelength ultraviolet light (PUVA), and synthetic retinoids or coal tar derivatives also is used. While mild to moderate cases can be treated somewhat effectively, more extensive cases are difficult and tend to be resistant to either topical therapy or ultraviolet phototherapy. Moreover, systemic use of traditional antipsoriatic drugs, or prolonged use of topical steroids, can lead to undesirable side effects or rebound worsening of psoriasis.

In particular, safety concerns for the patient with psoriasis, essentially a benign disorder, have been identified regarding the prolonged use of UVB and PUVA therapies. Psoralens intercalate within the DNA double helix and instigate DNA damage upon UVA irradiation. PUVA therapy is associated with increased risk for squamous cell carcinoma and malignant melanoma. PUVA-associated cancer risk increases with the number of treatments given. In addition, PUVA may increase skin cancer risk for patients who have a history of exposure to agents including ionizing radiation, methotrexate or arsenic as well as previous occurrences of basal or squamous cell carcinoma. UVB light, long recognized as a carcinogenic component of sunlight, is a standard anti-psoriasis therapy. UVB light directly interacts with DNA and is a potent carcinogen in animal systems.

The further development of treatments for psoriasis is of great interest.

SUMMARY OF THE INVENTION

Methods and compositions are provided for a safe and effective pharmacologic treatment for inflammatory disorders, including autoimmune diseases. Such disorders and diseases include, but are not limited to, psoriasis, rheumatoid arthritis, multiple sclerosis, scleroderma, systemic lupus erythematosus, Sjögren's syndrome, atopic dermatitis, asthma, and allergy. Target cells susceptible to the treatment include cells involved in instigating autoimmune reactions as well as those suffering or responding from the effects of autoimmune attack or inflammatory events. The treatment uses specific anti-ILK compounds that have minimal effects on the uninvolved tissues of the subject. Treatment includes the administration of agents that interfere with the ILK signaling pathway, including integrin linked kinase (ILK) blocking agents; compounds that otherwise prevent the binding of natural ILK ligands to ILK; or compounds that prevent expression of, or signaling through, ILK. Such a treatment is used alone as single therapy or in combination with a second therapy as an adjunct.

BRIEF DESCRIPTION OF THE DRAWINGS

FIGS. 1A-1F are sections depicting staining for the presence of integrin linked kinase in normal and psoriatic skin section.

FIGS. 2A-2D are sections depicting staining for the presence of integrin linked kinase, showing a correlation with psoriatic disease progression in epidermal keratinocytes and dermal vascular endothelium.

DETAILED DESCRIPTION OF THE EMBODIMENT

Figure 3:
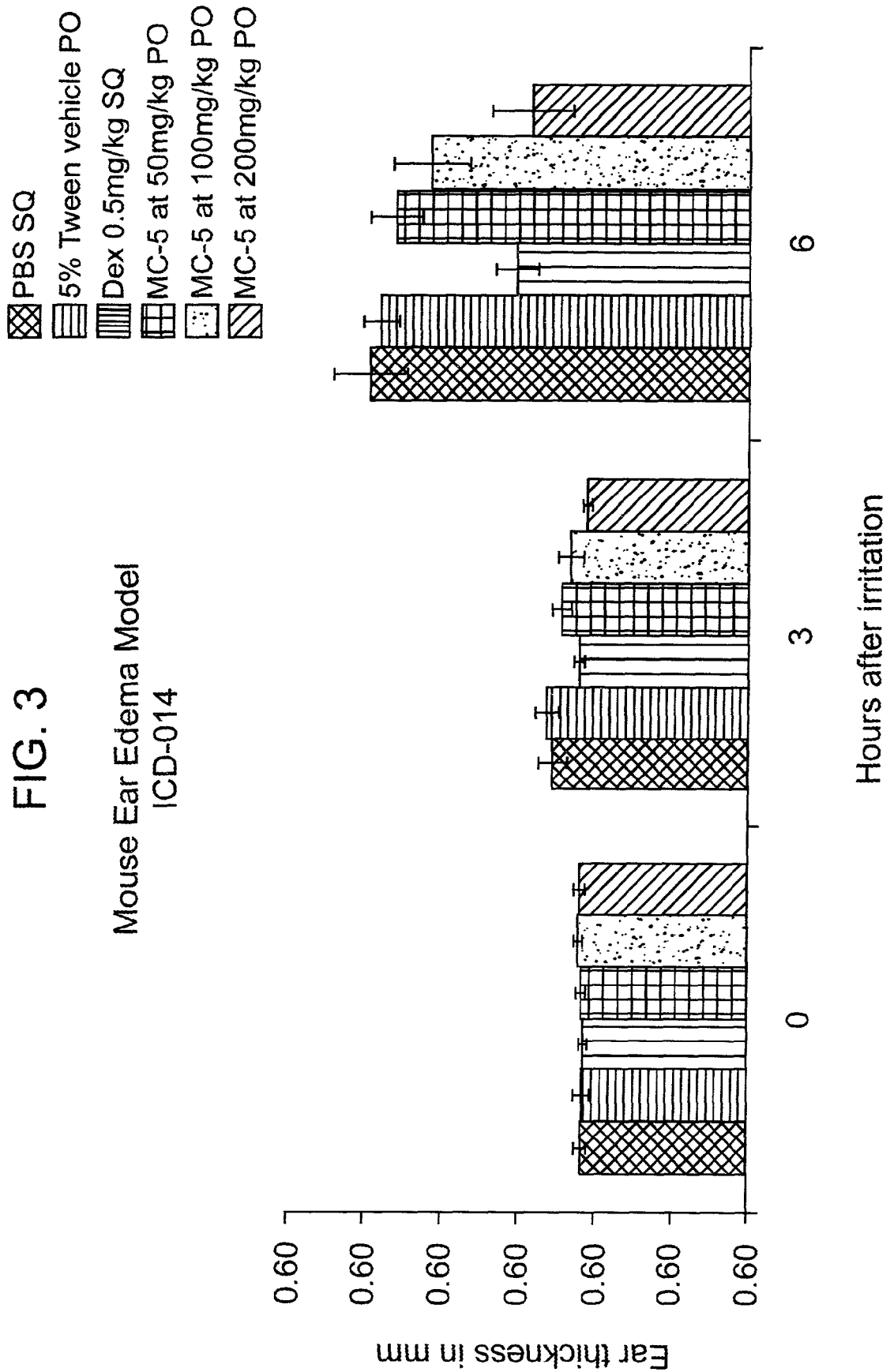
FIG. 3 depicts the anti-inflammatory activity of the anti-ILK compound MC-5 on edema.

Inflammatory disorders, including autoimmune diseases, are treated by administration of inhibitors of integrin linked kinase (ILK). Such disorders and diseases include, but are not limited to, psoriasis, rheumatoid arthritis, multiple sclerosis, scleroderma, systemic lupus erythematosus, Sjögren's syndrome, atopic dermatitis, asthma, and allergy. Cutaneous disorders are of particular interest. Target cells susceptible to the treatment include cells involved in instigating autoimmune reactions as well as those suffering or responding from the effects of autoimmune attack or inflammatory events.

ILK Modulating Agents

ILK is a 59 kDa serine/threonine kinase that associates with the cytoplasmic tails of $\beta1$ and $\beta3$ integrins. The enzymatic activity for ILK is modulated by the interaction of cells with the extracellular matrix component fibronectin, integrin clustering and a number of growth factors. Because of its intimate association with a wide variety of signaling pathways that have been directly or indirectly implicated in various pathological processes, ILK represents a therapeutic target for a variety clinical conditions including angiogenesis, cancer, inflammation and autoimmunity. The genetic sequence of human ILK is disclosed in U.S. Patent Nos. 6,013,782; and 6,001,622, herein incorporated by reference.

Overexpression of ILK results in a downregulation of E-cadherin expression, formation of a complex between $\beta$-catenin and the HMG transcription factor, LEF-1, translocation of .beta.-catenin to the nucleus, and transcriptional activation by this LEF-1/$\beta$-catenin complex. LEF-1 protein expression is rapidly modulated by cell detachment from the extracellular matrix, and LEF-1 protein levels are constitutively upregulated upon ILK overexpression. These effects are specific for ILK.

Agents that block ILK activity are used in the treatment of inflammatory disease, including psoriasis. Numerous agents are useful in reducing ILK activity, including agents that directly modulate ILK expression, e.g. anti-sense specific for ILK, ILK specific antibodies and analogs thereof, small organic molecules that block ILK catalytic or binding activity, etc.; and agents that affect ILK activity through direct or indirect modulation of [PtdIns(3,4,5)P$_3$] levels in a cell. For example, small molecule inhibitors of integrin linked kinase are described in U.S. Patent No. 6,214,813. Antisense inhibitors of ILK are described in U.S. Patent No. 6,177,273, each herein incorporated by reference.

Agents of interest for down-regulating ILK activity include direct blocking of [PtdIns(3,4,5)P$_3$] binding sites through competitive binding, steric hindrance, etc. Of particular interest are antibodies that bind to the PH domains, thereby blocking the site. Antibodies include fragments, e.g. F(Ab), F(Ab)', and other mimetics of the binding site. Such antibodies can be raised by immunization with the protein or the specific domain. Mimetics are identified by screening methods. Analogs of [PtdIns(3,4,5)P$_3$] that compete for binding sites but do not result in activation of ILK are also of interest.

Because ILK activity is upregulated by the presence of the lipid [PtdIns(3,4,5)P$_3$], the activity of ILK can be manipulated by agents that affect cellular levels of [Ptdins(3,4,5)P$_3$], or that block the binding of [PtdIns(3,4,5)P$_3$] to ILK. The amino acid sequence of ILK contains a sequence motif found in pleckstrin homology (PH) domains, which are involved in the binding of phosphatidylinositol phosphates. The activity of ILK is also down-regulated by inhibiting the activity of PI(3) kinase, thereby decreasing cellular levels of [Ptdins(3,4,5)P$_3$]. Agents of interest include inhibitors of PI(3) kinase, e.g. wortmannin, LY294002, etc. Physiologically effective levels of wortmannin range from about 10 to 1000 nM, usually from about 100 to 500 nM, and optimally at about 200 nM. Physiologically effective levels of LY294002 range from about 1 to 500 µM, usually from about 25 to 100 µM, and optimally at about 50 µM. The inhibitors are administered in vivo or in vitro at a dose sufficient to provide for these concentrations in the target tissue.

Drug screening can be used to identify agents that modulate ILK function. One can identify ligands or substrates that inhibit the action of ILK. A wide variety of assays may be used for this purpose, including labeled in vitro protein-protein binding assays, electrophoretic mobility shift assays, immunoassays for protein binding, and the like. Knowledge of the 3-dimensional structure of ILK, derived from crystallization of purified recombinant ILK protein, leads to the rational design of small drugs that specifically inhibit ILK activity. These drugs may be directed at specific domains of ILK, e.g. the kinase catalytic domain, ankyrin repeat domains, pleckstrin homology domains, etc. Among the agents of interest for drug screening are those that interfere with the binding of cytoplasmic integrin tails to ILK; the kinase activity of ILK; binding of [PtdIns(3,4,5)P$_3$] to the PH domains of ILK and agents that inhibit the production of [PtdIns(3,4,5)P$_3$] by PI(3) kinase.

The term "agent" as used herein describes any molecule, e.g. protein or pharmaceutical, with the capability of altering the physiological function of ILK. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Assays of interest may detect agents that block ILK function, such as integrin binding, kinase activity, down regulation of E-cadherin, up regulation of LEF-1, binding properties, etc. For example, an expression construct comprising a ILK gene may be introduced into a cell line under conditions that allow expression. The level of ILK activity is determined by a functional assay, as previously described. In one screening assay, candidate agents are added, and the formation of fibronectin matrix is detected. In another assay, the ability of candidate agents to enhance ILK function is determined.

Methods of Treatment

The subject methods are used for prophylactic or therapeutic purposes to treat inflammatory diseases, including cutaneous inflammatory diseases, e.g. psoriasis. As used herein, the term "treating" is used to refer to both prevention of disease, and treatment of pre-existing conditions. While treatment during early stages is desirable, the adverse symptoms of the disease may be at least partially alleviated by treatment during later stages.

In practicing the method of treatment or use of the present invention, a therapeutically effective amount of an ILK inhibitor is administered to a subject afflicted with an inflammatory disease. The inhibitor may be administered in accordance with the method of the invention either alone of in combination with other known therapies. When co-administered with one or more other therapies, the inhibitor may be administered either simultaneously with the other treatment(s), or sequentially. If administered sequentially, the attending physician will decide on the appropriate sequence of administration, which may be before or after a second therapy.

To ameliorate inflammatory/autoimmune diseases such as psoriasis, inhibitors of ILK are administered by an appropriate means including, but not limited to, oral, intravenous, subcutaneous, intramuscular or topical routes. The local delivery, such as topical, of an ILK inhibitor provides high concentrations at the treatment site while lowering the likelihood of unwanted non-specific or other undesirable effects that might be associated with systemic delivery of such compounds.

For the local delivery of ILK inhibitors for psoriasis and other cutaneous inflammatory or autoimmune conditions, the compounds may be administered in excipients containing concentrations of about 0.01 to about 10 mg/ml directly applied to the skin. If systemic delivery is required, a dose range of 0.1 mg/kg to 100 mg/kg body weight, preferably less than 10 mg/kg, is administered. The ILK inhibitor may be given up to 3 times daily. Oral delivery may be given in tablets, capsules, liquid suspensions or solutions.

The dose of ILK inhibitor in the pharmaceutical composition of the present invention will depend upon the nature and severity of the condition being treated, and on the nature of prior treatments which the patent has undergone. Ultimately, the attending physician will decide the dose with which to treat each individual patient. Initially, the attending physician may administer low doses and observe the patient's response. Larger doses may be administered until the optimal therapeutic effect is obtained for the patient, and at that point the dosage is not increased further.

Psoriasis

Suitable animal models exist for determination of appropriate dosage, for example see U.S. Pat. No. 6,187,993, issued Feb. 13, 2001. However the efficacy of a therapeutic effect for different mammals varies widely, for example doses typically are 20, 30 or even 40 times smaller (per unit body weight) in man than in the rat. Similarly the mode of administration can have a large effect on dosage. Scoring of the disease severity is based on physical appearance and ear thickness. Symptoms include erythema on one or more locations, generally first appearing on the ears and face; and scaling over the body surface. Severe scaling is defined as covering more than about 20% of the surface of the animal. Measurement of ear thickness is conventional, using a micrometer, etc. After a period of time sufficient for the development or regression of the disease, the animals are assessed for impact of the treatment, by visual, histological, immunohistological, and other assays suitable for determining effectiveness of the treatment. The results may be expressed on a semi-quantitative or quantitative scale in order to provide a basis for statistical analysis of the results.

The ILK inhibitors may be administered before, concurrently with, or after a second treatment for psoriasis, and may be formulated separately or in combination. Examples of known treatment for psoriasis is provided in Table 1.

TABLE 1

| THERAPY | NOTES |
|---------|-------|
| SYSTEMIC TREATMENTS | |
| Antibiotics, antimicrobials | Infections may worsen (flare) psoriasis |
| Cyclosporine | Suppresses the body's immune system; use for more than one year not recommended |
| Methotrexate | Effective in psoriasis and psoriatic arthritis; Lifetime cumulative dose of 4.5 grams has been associated with up to 25% risk of liver/cirrhosis/fibrosis |
| Hydroxyurea, NSAIDS, Sulfasalazine, 6-thioguanine | |
| Retinoids—acitretin, etretinate, isotretinoin | Etretinate, labeled for psoriasis, has been replaced by acitretin |
| ULTRAVIOLET LIGHT | |
| Hospitalization, Outpatient day treatment | For severe psoriasis: Intensive nurse administered therapy of day-long UV and prescription topicals for 30 days or more |
| Phototherapy (UVB) | Minimum 20–40 treatments to clear psoriasis; additional treatments may prolong clearance |
| Photochemotherapy (PUVA) | Combines ingestion, soaking, or painting with psoralen medication before exposure to UVA light. Minimum 20 treatments to produce substantial clearing; additional to prolong clearance |
| Home phototherapy (UVB) | Durable medical equipment for home use to prolong clearance in physician-selected patients. |

TABLE 1-continued

| THERAPY | NOTES |
|---|---|
| SYSTEMIC TREATMENTS | |
| TOPICAL AND INTRALESIONAL THERAPY | |
| Anthralin | Compounded in various strengths, can be combined with UV exposure |
| Calcipotriene | Topical vitamin D is first in this class to be approved for psoriasis |
| Coal Tar | Compounded in various strengths, can be combined with UV exposure |
| Corticosteroids—low strength | Applied to skin |
| Corticosteroids—moderate to potent | Various potencies, applied to skin, injected into lesions, or taken orally |
| Emollients | Preserves skin flexibility |
| Keratolytics—salicylic acid | Compounded in various strengths, used with tar or emollients |
| Tazarotene | First topical vitamin A derivative approved for psoriasis |

Other Inflammatory Conditions

Degenerative joint diseases may be inflammatory, as with seronegative spondylarthropathies, e.g. ankylosing spondylitis and reactive arthritis; rheumatoid arthritis; gout; and systemic lupus erythematosus. The degenerative joint diseases have a common feature, in that the cartilage of the joint is eroded, eventually exposing the bone surface. Destruction of cartilage begins with the degradation of proteoglycan, mediated by enzymes such as stromelysin and collagenase, resulting in the loss of the ability to resist compressive stress. Alterations in the expression of adhesion molecules, such as CD44 (Swissprot P22511), ICAM-1 (Swissprot P05362), and extracellular matrix protein, such as fibronectin and tenascin, follow. Eventually fibrous collagens are attacked by metalloproteases, and when the collagenous microskeleton is lost, repair by regeneration is impossible.

For example, rheumatoid arthritis (RA) is a chronic autoimmune inflammatory synovitis affecting 0.8% of the world population. Current therapy for RA utilizes therapeutic agents that non-specifically suppress or modulate immune function. Such therapeutics, including the recently developed TNFα antagonists, are not fundamentally curative, and disease activity rapidly returns following discontinuation of therapy. Tremendous clinical need exists for fundamentally curative therapies that do not cause systemic immune suppression or modulation. There is significant immunological activity within the synovium during the course of inflammatory arthritis. While treatment during early stages is desirable, the adverse symptoms of the disease may be at least partially alleviated by treatment during later stages. Clinical indices for the severity of arthritis include pain, swelling, fatigue and morning stiffness, and may be quantitatively monitored by Pannus criteria. Disease progression in animal models may be followed by measurement of affected joint inflammation. Therapy for inflammatory arthritis may combine the subject treatment with conventional NSAID treatment.

A quantitative increase in myelin-autoreactive T cells with the capacity to secrete IFN-gamma is associated with the pathogenesis of MS and EAE, suggesting that autoimmune inducer/helper T lymphocytes in the peripheral blood of MS patients may initiate and/or regulate the demyelination process in patients with MS. The overt disease is associated with muscle weakness, loss of abdominal reflexes, visual defects and paresthesias. During the presymptomatic period there is infiltration of leukocytes into the cerebrospinal fluid, inflammation and demyelination. Family histories and the presence of the HLA haplotype DRB1*1501, DQA1*0102, DQB1*0602 are indicative of a susceptibility to the disease. Markers that may be monitored for disease progression are the presence of antibodies in the cerebrospinal fluid, "evoked potentials" seen by electroencephalography in the visual cortex and brainstem, and the presence of spinal cord defects by MRI or computerized tomography. Treatment during the early stages of the disease will slow down or arrest the further loss of neural function.

Human IDDM is a cell-mediated autoimmune disorder leading to destruction of insulin-secreting beta cells and overt hyperglycemia. T lymphocytes invade the islets of Langerhans, and specifically destroy insulin-producing β-cells. The depletion of β-cells results in an inability to regulate levels of glucose in the blood. Overt diabetes occurs when the level of glucose in the blood rises above a specific level, usually about 250 mg/dl. In humans a long presymptomatic period precedes the onset of diabetes. During this period there is a gradual loss of pancreatic beta cell function. The disease progression may be monitored in individuals diagnosed by family history and genetic analysis as being susceptible. The most important genetic effect is seen with genes of the major histocompatibility locus (IDDM1), although other loci, including the insulin gene region (IDDM2) also show linkage to the disease (see Davies et al, supra and Kennedy et al. (1995) Nature Genetics 9:293□298).

Markers that may be evaluated during the presymptomatic stage are the presence of insulitis in the pancreas, the level and frequency of islet cell antibodies, islet cell surface antibodies, aberrant expression of Class II MHC molecules on pancreatic beta cells, glucose concentration in the blood, and the plasma concentration of insulin. An increase in the number of T lymphocytes in the pancreas, islet cell antibodies and blood glucose is indicative of the disease, as is a decrease in insulin concentration. After the onset of overt diabetes, patients with residual beta cell function, evidenced by the plasma persistence of insulin C-peptide, may also benefit from the subject treatment, to prevent further loss of function.

Formulations

The compounds of this invention can be incorporated into a variety of formulations for therapeutic administration. Administration of an ILK inhibitor may be by delivery using any appropriate means including, but not limited to, systemic, local, or even direct application to the target tissue. Local delivery of an ILK inhibitor provides a high local concentration while reducing the likelihood of non-specific anti-angiogenic or other undesirable side effects that may follow systemic administration of an ILK inhibitor.

For local application, a range of about 0.05 to 0.2 or about 0.5 mg/ml of an ILK inhibitor in an appropriate formulation is administrated dermally. For systemic application, a range of 1 mg/kg to 100 mg/kg body weight, preferably less than about 10 mg/kg is administered.

The compounds of the present invention are formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, etc., administration. The ILK may be systemic after administration or may be localized by the use of an implant that acts to retain the active dose at the site of implantation.

The compounds of the present invention can be administered alone, in combination with each other, or they can be used in combination with other known compounds and therapies. In pharmaceutical dosage forms, the compounds may be administered in the form of their pharmaceutically acceptable salts, or they may also be used alone or in appropriate association, as well as in combination with other pharmaceutically active compounds.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

For dermal administration, the compositions of the invention may optionally comprise other skin benefit materials. These include estradiol; progesterone; pregnanalone; coenzyme Q10; methylsolanomethane (MSM); copper peptide (copper extract); plankton extract (phytosome); transforming growth factor beta 1 (TGF-β1); glycolic acid; kojic acid; ascorbyl palmitate; all-trans-retinol; azaleic acid; salicylic acid; broparoestrol; estrone; adrostenedione; androstanediols; etc. The steroids will generally present at a concentration of less than about 2% of the total by weight of the composition, while the other skin benefit materials may be present at higher levels, for example as much as 10 to 15%.

The compositions of the invention comprise a cosmetically acceptable vehicle to act as a dilutant, dispersant or carrier for the ILK inhibitor, so as to facilitate its distribution when the composition is applied to the skin. Vehicles other than or in addition to water can include liquid or solid emollients, solvents, humectants, thickeners and powders.

The compositions may be in the form of aqueous, aqueous/alcoholic or oily solutions; dispersions of the lotion or serum type; anhydrous or lipophilic gels; emulsions of liquid or semi-liquid consistency, which are obtained by dispersion of a fatty phase in an aqueous phase (O/W) or conversely (W/O); or suspensions or emulsions of smooth, semi-solid or solid consistency of the cream or gel type. These compositions are formulated according to the usual techniques as are well known to this art.

When the compositions of the invention are formulated as an emulsion, the proportion of the fatty phase may range from 5% to 80% by weight, and preferably from 5% to 50% by weight, relative to the total weight of the composition. Oils, emulsifiers and co-emulsifiers incorporated in the composition in emulsion form are selected from among those used conventionally in the cosmetic or dermatological field. The emulsifer and coemulsifier may be present in the composition at a proportion ranging from 0.3% to 30% by weight, and preferably from 0.5% to 20% by weight, relative to the total weight of the composition.

When the compositions of the invention are formulated as an oily solution or gel, the fatty phase may constitute more than 90% of the total weight of the composition.

The compositions of the invention may also contain additives and adjuvants which are conventional in the pharmaceutical or dermatological field, such as hydrophilic or lipophilic gelling agents, hydrophilic or lipophilic active agents, preservatives, antioxidants, solvents, fragrances, fillers, bactericides, odor absorbers and dyestuffs or colorants. The amounts of these various additives and adjuvants are those conventionally used in the field, and, for example, range from 0.01% to 10% of the total weight of the composition. Depending on their nature, these additives and adjuvants may be introduced into the fatty phase, into the aqueous phase.

Exemplary oils which may be used according to this invention include mineral oils (liquid petrolatum), plant oils (liquid fraction of karite butter, sunflower oil), animal oils (perhydrosqualen(e), synthetic oils (purcellin oil), silicone oils (cyclomethicone) and fluoro oils (perfluoropolyethers). Fatty alcohols, fatty acids (stearic acid) and waxes (paraffin wax, carnauba wax and beeswax) may also be used as fats.

Emulsifiers which may be used include glyceryl stearate, polysorbate 60, PEG-6/PEG-32/glycol stearate mixture, etc. Solvents which may be used include the lower alcohols, in particular ethanol and isopropanol, and propylene glycol.

Hydrophilic gelling agents include carboxyvinyl polymers (carbomer), acrylic copolymers such as acrylate/alkylacrylate copolymers, polyacrylamides, polysaccharides, such as hydroxypropylcellulose, natural gums and clays, and, as lipophilic gelling agents, representative are the modified clays such as bentones, fatty acid metal salts such as aluminum stearates and hydrophobic silica, or ethylcellulose and polyethylene.

An oil or oily material may be present, together with an emollient to provide either a water-in-oil emulsion or an oil-in-water emulsion, depending largely on the average hydrophilic-lipophilic balance (HLB) of the emollient employed. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

In use, a small quantity of the composition, for example from 1 to 100 ml, is applied to exposed areas of the skin, from a suitable container or applicator and, if necessary, it is then spread over and/or rubbed into the skin using the hand or fingers or a suitable device.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

It is to be understood that this invention is not limited to the particular methodology, protocols, cell lines, animal species or genera, constructs, and reagents described, as such may vary. It is also to be understood that the terminology used herein is for the purpose of describing particular embodiments only, and is not intended to limit the scope of the present invention which scope will be determined by the language in the claims.

It must be noted that as used herein and in the appended claims, the singular forms "a", "and", and "the" include plural referents unless the context clearly dictates otherwise. Thus, for example, reference to "a mouse" includes a plurality of such mice and reference to "the cytokine" includes reference to one or more cytokines and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for all relevant purposes, e.g., the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Example 1

ILK Expression is High in Human Psoriatic Skin as Compared to Normal Skin

It was unknown whether the activity or expression levels of ILK are altered in human pathologic states such as autoimmune diseases. Skin samples were obtained from a human subject with healthy skin and from patients suffering from the immune-mediated condition psoriasis. Psoriasis is a complex inflammatory autoimmune condition characterized by an abnormal activation of skin T lymphocytes, dermal and epidermal infiltration by various types of leukocytes, hyperproliferation of keratinocytes and pronounced angiogenic activity within the dermal vasculature. The thickness of the epidermal layer within psoriatic plaques is dramatically greater than that of normal skin of healthy individuals or the uninvolved skin of the psoriasis patient.

To test for ILK expression, skin preparations were processed using routine formalin-fixation and paraffin embedding techniques. Sections were cut and treated with antigen retrieval methodology and stained with a rabbit anti-ILK polyclonal antibody (catalogue #06-592, Upstate Biotechnology, Lake Placid N.Y.). Sections were then incubated with peroxidase-conjugated goat anti-rabbit polyclonal antibody. Slides were then developed using standard techniques.

For normal skin (shown in FIG. 1), a low level of ILK expression was evident in the supra-basal layers of skin keratinocytes that were almost certainly undergoing the process of terminal differentiation. The staining intensity for ILK was more intense for keratinocytes near the outer keratin layer. Little or no ILK staining occurred for the dermal vascular endothelium. In contrast, staining for ILK was highly intense for the hyper-proliferative keratinocytes within the plaques of the two psoriasis patients analyzed. Within the dermal region of psoriatic patient plaques, cells comprising the vasculature stained strongly for ILK. Further, some of the inflammatory cells present within the dermal region stained positively for ILK. Overall, in contrast to normal skin, ILK was expressed at much higher levels within the epidermal and dermal regions within skin plaques of patients with psoriasis.

Example 2

Expression of ILK is Psoriatic Tissue Correlates With Severity of Disease

The expression of ILK within psoriatic skin was evaluated for a series of plaque biopsy samples obtained from a patient over a 3-month period. The presence and expression pattern of ILK was evaluated by immunohistological analyses. All sections were stained at the same time. For psoriasis, the disease-state can be gauged by the relative thickness of the epidermis.

For the series of biopsy samples evaluated, expression levels of ILK closely paralleled the psoriasis disease-state at the tissue level.

The first sample (FIG. 2A), was obtained at screening while the patient was experiencing active disease. Staining for ILK was intense for the keratinocytes within the target plaque. Within the dermal region of the plaque, cells within the vasculature as well as cells that had infiltrated the region also stained strongly for ILK.

The second sample (FIG. 2B) was obtained one month later, a time when disease activity had further intensified. ILK staining intensity was this sample was much stronger than for the first sample.

The third sample (FIG. 2C) was taken approximately 4 weeks after sample B, a time during which this subject was exhibiting an improvement in their disease and a reduction in epidermal thickness. For this sample there was a correspondent reduction in ILK staining intensity, both for the epidermal keratinocytes and within cells of the dermal vasculature.

Sample 4 (FIG. 2D), was obtained 3 months after sample 1, at a time that the subject was experiencing a flare in disease activity. Epidermal thickness for sample 4 was greater than that of sample 3. At this time, an increase in ILK staining intensity was evident within the dermal vasculature and cellular infiltrate as well as for the epidermal keratinocytes. Thus, expression levels of ILK within the psoriatic plaque varied with disease activity with high ILK expression correlating with symptoms of active disease.

Example 3

Anti-Inflammatory Effect Of ILK-Inhibition

The anti-inflammatory activity of the anti-ILK compound MC-5 was demonstrated in an acute mouse ear-swelling edema model. To induce this inflammatory experimental condition, mice are treated topically on the surface of an ear with tetra phorbol ester (TPA). Application of TPA in such a manner produces a rapid increase in ear thickness caused by fluid buildup and the infiltration of the tissue by inflammatory cells.

Different doses of MC-5 were given orally at the same time as an active amount of TPA (FIG. 3). Ear measurements performed 6 hours after these treatments showed that a dose of MC-5 of 200 mg/kg almost completely prevented the increase in ear swelling stimulated by TPA. The effect of this dose of MC-5 on this response was comparable to that produced by dexamethasone, a well-characterized and potent anti-inflammatory agent. Thus, a compound that is known to inhibit the activity of ILK in vitro can also affect the development of symptoms of an experimental inflammatory skin condition in vivo.

Example 4

Anti-ILK Compound Inhibits Influx of Neutrophils into Site of Inflammation

Administration of certain pro-inflammatory agents, such as zymosan, into the peritoneal cavity of mice elicits a rapid influx of neutrophils into this region. The migration of these cells into the peritoneal cavity requires the coordinate interaction of cytokines, chemokines and cell adhesion molecules. Such a system is used to evaluate the action of compounds with potential for modifying the migration of cells in response to pro-inflammatory stimuli.

When zymosan was administered to mice, peritoneal cavity neutrophil numbers increased by approximately 4-fold within 4 hours. However, if MC-5 was given orally at 200 mg/kg at the time of zymosan administration cells numbers within the peritoneal cavity were equivalent to those of animals that received a saline control solvent 4 hours before. Thus, a compound with specific in vitro anti-ILK activity can affect the influx of cells into a tissue following the delivery of a strong pro-inflammatory signal in vivo.

What is claimed is:

1. A method for treating psoriasis, the method comprising: administering an effective amount of an inhibitor of integrin linked kinase (ILK) to a psoriatic lesion, wherein expression of ILK in psoriatic tissue correlates with severity of disease, and said ILK inhibitor is a small organic molecule that inhibits ILK activity.

2. The method according to claim 1, further comprising the step of administering a second therapy for psoriasis.

3. The method according to claim 2, wherein second therapy is selected from the group consisting of systemic therapy, ultraviolet light therapy, and topical therapy.

4. The method according to claim 2, wherein said second therapy is selected from the group consisting of antibiotics, antimicrobials, cyclosporine, methotrexate, hydroxyurea, NSAIDs, sulfasalazine, 6-thioguanine, acitretin, etretinate, isotretinoin; UVB phototherapy, photochemotherapy (PUVA), anthralin, calcipotriene, coal tar, corticosteroids, and tazarotene.

5. The method according to claim 1, wherein said ILK inhibitor is administered systemically.

6. The method according to claim 1, wherein said ILK inhibitor is administered dermally.

7. A method for treating psoriasis, the method comprising: staining to determine the expression of integrin linked kinase in a psoriatic lesion, and where expression of ILK in said psoriatic lesion correlates with severity of disease;
administering an effective amount of an inhibitor of integrin linked kinase (ILK), wherein said ILK inhibitor is a small organic molecule that inhibits ILK activity.

* * * * *